United States Patent [19]

Yee

[11] Patent Number: 4,886,493
[45] Date of Patent: Dec. 12, 1989

[54] MEDICAL APPLICATOR PROCESS

[76] Inventor: Jordan Yee, 517 Getzville Rd., Amherst, N.Y. 14226

[21] Appl. No.: 111,213

[22] Filed: Oct. 22, 1987

[51] Int. Cl.$^4$ ............................................. A61M 31/00
[52] U.S. Cl. .......................................... 604/54; 604/49
[58] Field of Search ...................... 604/24, 26, 49, 54; 128/200.14, 200.22

[56] References Cited

U.S. PATENT DOCUMENTS

| | | | |
|---|---|---|---|
| 598,286 | 2/1898 | Curran | 604/54 X |
| 645,566 | 3/1900 | Murphey | 604/58 X |
| 2,470,297 | 5/1949 | Fields | 604/58 X |
| 2,672,141 | 3/1954 | Filger | 128/200.22 |
| 3,747,595 | 7/1973 | Grossan | 604/54 X |
| 4,300,557 | 11/1981 | Refojo et al. | 604/49 X |
| 4,402,684 | 9/1983 | Jessup | 128/200.22 X |
| 4,479,800 | 10/1984 | Chester | 604/187 |
| 4,737,141 | 4/1988 | Spits | 604/54 X |

OTHER PUBLICATIONS

Robert E. Ryan, Jr. M.D. et al., "Sphenopalatine Ganglion Neuralgia and Cluster Headache", Headache 17:7-9, Mar. 1977.

Kittrelle JP. et al., "Cluster Headache and Local Anesthetic Abortive Agents" Arch. Neurol.-vol. 42, May, 1985, pp. 496-498.

Primary Examiner—Danton D. DeMille
Assistant Examiner—Sam Rimell
Attorney, Agent, or Firm—James J. Ralabate

[57] ABSTRACT

An applicator and process for accomplishing the Sphenopalatine Ganglion Block wherein an extended tube of a fixed length and width is used. The amount of medication administered is critical and should be between about 1/16 c.c. and about ⅜ c.c.; an amount below this range will be substantially ineffective, and above this range could have serious side effects. The applicator tube is flexible and must have depth indicators for proper usage.

8 Claims, 1 Drawing Sheet

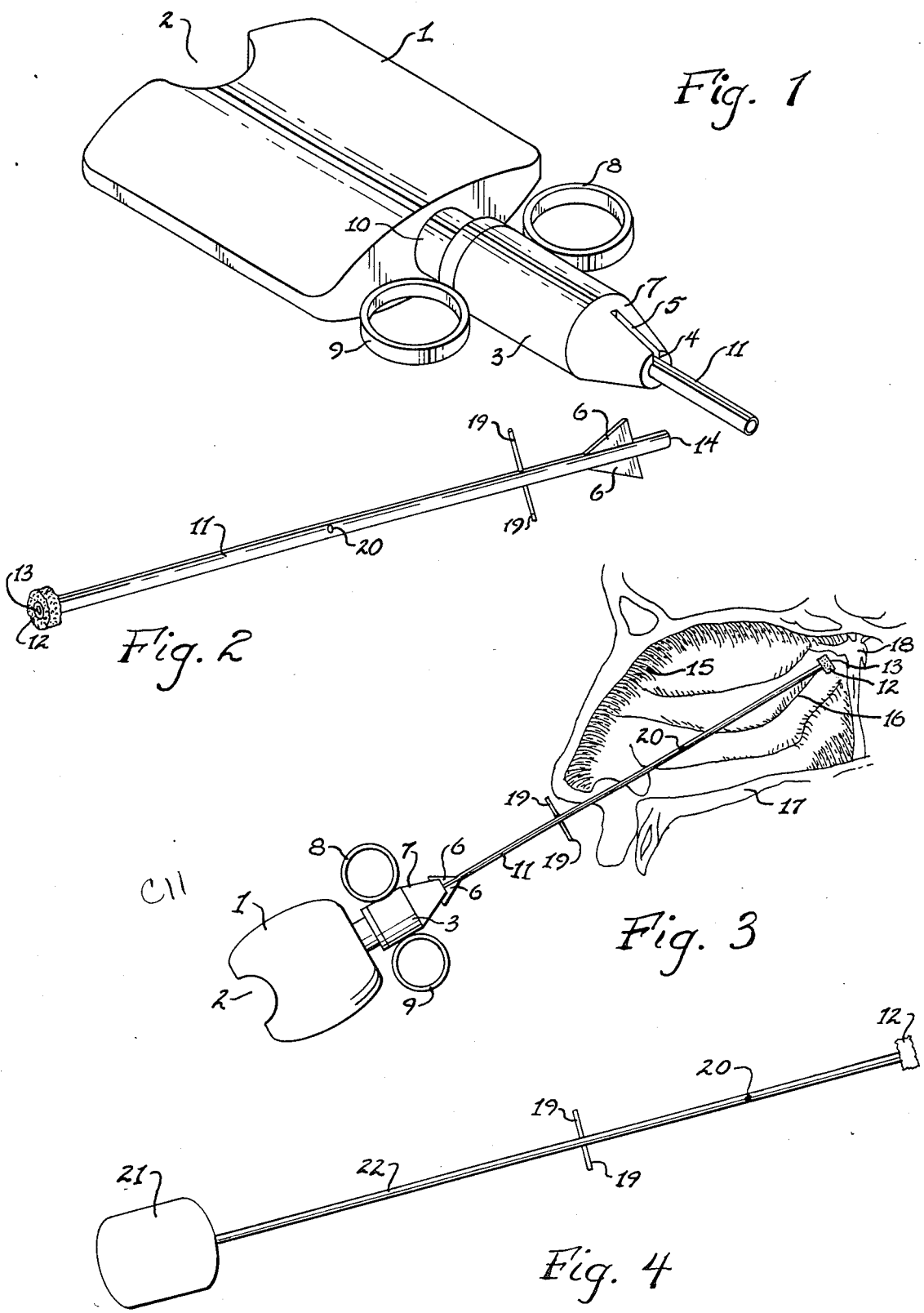

MEDICAL APPLICATOR PROCESS

This invention relates to an applicator and process for the treatment of pain and, more specifically, for an applicator and process to accomplish the Sphenopalatine Ganglion Block in a patient.

BACKGROUND OF THE INVENTION

The Sphenopalatine Ganglion Block (hereinafter S.P.G.B.) was the first reported by Greenfield Sluder, clinical professor and director of the Department of Otolaryngology at Washington University, School of Medicine, St. Louis, Mo. This procedure was described as a non-invasive ganglion block for various chronic pain with no prolonged side effects. It required skillfully trained physicians to do this procedure in a medical environment. References dealing with this medical procedure are as follows:

(A) Reder M A, Humanson A S, Reder M. Sphenopalatine ganglion block in treatment of acute and chronic pain. In: Hendler N H, Long D M, Wise T N, eds. Diagonosis and treatment of chronic pain. Boston: John Wright, 1982: 97-108

(B) Ruskin S L. Contributions to the study of the sphenopalatine ganglion. Laryngoscope 1925; 35: 87-108

(C) Berger J J. et al., Does Topical Anesthesia of the Sphenopalatine Ganglion with Cocaine or Lidocaine Relieve Low Back Pain? Anesth Analg 1986; 65: 700-2

(D) Procacci P, Francini F, Loppi M, Maresea M. Cutaneous pain threshold changes after sympathetic block in reflex dystrophies. Pain 1975; 1: 167-75

(E) Ruskin A P. Sphenopalatine (nasal) ganglion: Remote effects including "psychosomatic" symptoms, rage reaction, pain and spasm. Arch Phys Med Rehabil 1979; 60: 353-9

(F) Kittrelle J P. et al., Cluster Headache local Anesthetic Abortive Agents. Arch Neurol-Vol 42, May 1985 496-498

(G) VanDyke C, Jatlow P. Ungerer J. Varash P, Byck R. Cocaine and lidocaine have similar psychological effects after intranasal application. Life Sci 1979; 24: 271-4

(H) Sluder G. The Anatomical and clinical relations of the sphenopalatine ganglion to the nose. NY State J. Med 1909; 90: 293-298

(I) Sluder G. The syndrome of sphenopalatine ganglion neuralgia. Am J Med Sci 1910; 111: 868-878

(J) Sluder G. Nasal Neurology, Headaches and Eye Disorders. St. Louis, CV Mosby, 1927

(K) Robert E. Ryan Jr. M.D., George W. Facer, M.D., Sphenopalatine Ganglion Neuralgia and Cluster Headache: Comparisons, Contrasts, and Treatment. Headache 17: 7-9, March 1977

The use of the term "block" or "blockade" in this disclosure means to stop the nerve impulse, or to stop the painful activity that is caused by the firing of the nerve treated, and also the correction of any adverse effect on the human body that is caused by the increased activity of the nerve center.

The sphenopalatine ganglion, located in the pterygopalatine fossa posterior to the middle turbinate, is separated from the nasal passage by a thin 1 to 5 mm layer of connective tissue and mucous membrane. Local anesthetics (such as lidocaine) topically applied to the appropriate region of the nasal passage can readily diffuse into the ganglion. The sphenopalatine ganglion has major branches to the trigeminal nerve, the facial nerve and the cartoid plexus, the latter communicating directly with the superior cervical sympathetic ganglion. The sphenopalatine ganglion has sensory, visceral motor (para sympathetic), and sympathetic functions.

The sensory root is connected with the maxillary division of the trigeminal nerve, these fibers modulate the rostral transmissions of pain information from the periphery, acting like a gate-control mechanism.

Blockade of the sphenopalatine ganglion may inhibit this baseline tonic activity and in so doing, close the gate, acting through the same mechanism as that proposed to explain the analgesia of transcutaneous nerve stimulation, but at a higher lever in the central nervous system. This connection may explain the success of sphenopalatine ganglion block in tic douloureux. Parasympathetic activity of the sphenopalatine ganglion is mediated via the superficial petrosal nerve; the branches going to the lacrimal gland may explain the excessive lacrimation associated with stimulation of the sphenopalatine ganglion.

The sympathetic root of the sphenopalatine ganglion is the great deep petrosal nerve which is essentially an extension of the cervical sympathetic chain via the cartoid plexus. Cell bodies in the ventral horn of the thoracolumbar spinal cord send fibers, either directly or via cervical ganglion synapse, some of which course through the sphenopalatine ganglion on their way to the periphery, and others of which synapse in the sphenopalatine ganglion. There are also sensory afferent cells with cell bodies in dorsal roots of the spinal cord which synapse on interneurons and ventral horn sympathetic cells reflexively. The peripheral axons of these fibers course through the sphenopalatine ganglion. Anatomically, this interposes the sphenopalatine ganglion in a sympathetic reflex arc which loops between the thoracolumbar spinal cord and the head.

This procedure appears to be beneficial in many patients with pain, in particular, that due to muscle spasm, vascospasm, neuralgia, reflex sympathetic dystrophy and chronic low back pain of multiple etiology (muscular, discogenic, arthritic, and metastatic), external cricoidynia, lower jaw toothache, glossodynia, earache in case of Eustachian tube and middle ear lesions, earache secondary to cancer of the larynx, the pain of laryngeal tuberculosis, relief of spasm of the face and upper respiratory tract, all syphilitic headache, malarial headache, cluster headache, ophthalmic migraine, dysmenorrhea, intercostal pain (neuralgia), gastric pain, nausea and diarrhea, myalgias of the neck muscles, sciatica, maxillary neuralgia, sensory facial neuralgia, pain in the upper teeth and sensation as through teeth were too long, tooth extraction or other dental procedures, feeling of foreign body in the throat, persistant itching in the external ear canal, herpes zoster oticus, taste disturbances, atypical facial pain, tic douloureux, cervical arthritis, myofascial syndrome, peripheral neuropathy, post-herpetic neuralgia, fracture secondary to osteoporosis, extremity arthritis and various arthritic conditions and lumbosacral strain. Since the pain transmission pathway for these various conditions have a similar relationship to the SPG, therefore, the impact of the SPG block should be equivalent (see discussion above). Further indication not related to pain control is the control of rage reaction and improvement of depression in the psychiatric patient. While the SPG block is effective in controlling chronic pain, it is accomplished by medical professionals by using the pledget delivery method. In the pledget method, usually two cotton-tipped applicators are inserted into one of the two nostrils of the patient (there are two SPG, one on the left, one on the right) and using the middle turbinate as an anatomical landmark guideline, the two applicators are pushed upward until they contact the desired area in a blind approach. The success rate of the procedure is directly proportional to the experience of the physician. Lidocaine is applied on the cotton of the applicators and is then applied to the SPG area via the soaked cotton. This method delivers an imprecise amount of medication to the area being treated and if in excess, can cause undesirable side effects such as throat irritation or systemic hypotension leading to shock and induce trauma to the nose. In addition, use of the pledget method could deliver less than an effective amount of medication, or miss the appropriate area to do this SPG block therefore resulting in failure of the desired results. These cotton-tipped applicators must be retained inside the patient's nose for a period of at least thirty minutes and often cause severe pain. It is necessary that the pledget method be conducted by a medical doctor who is trained as a medical specialist in the areas such as: ear, nose and throat, rehabilitation medicine or neurology in a hospital, doctor's office, clinic or other medical environments. There is therefore a pressing need for a procedure to accomplish the SPG block with applicators other than the heretofore used cotton-tipped applicators.

There are many known medical applicators as described in prior art U.S. Pat. Nos. 475,035; 2,672,141; 3,369,543; 4,402,684 and 4,405,308. In 475,035 (Van Woud) an atomizer is disclosed for dispensing medication into the nose. This type of device, however, would be ineffective in the S.P.G.B. procedure because like U.S. Pat. No. 2,672,141 (Filger) the nasal spray from the opening of the nostril will not get to the appropriate area to effect the SPG block. The anesthetic liquid from these devices most likely would drip down into the throat impairing the swallowing reflex and causing fluid to go into the lungs. It is important in the S.P.G.B. procedure that a precise quantity of medication be delivered to the treated area, a dead end area at the back of the nose measuring above 5.5 cm away from the nares. Neither Van Woud's or Filger's device is capable of this requirement. Thus, neither device is suitable for the present procedure.

In U.S. Pat. No. 3,369,543 to Ronco, a hollow casing type medical applicator is disclosed. In Ronco's device a hollow casing of an elongated deformable material with an open end is used to dispense medicine from the casing. A wick is used in the open end to provide capillary transmission of the medicine to the area to be treated. The size of casing 11 of Ronco would render it non-functional for interior nasal applications. Ronco's device is intended for treatment of external areas of the body and would not be capable of delivering a precise amount of medication to the interior of the nose to accomplish the SPG block.

In U.S. Pat. Nos. 4,402,684 (Jessup 1) and 4,405,308 (Jessup 2) anesthesia devices are disclosed using cannulas. These devices are used for trachea anesthesia and do not produce a single "shotgun-like" jetstream spray at a measured amount or volume of medication as required in the SPG block procedure for acceptable results.

Therefore, none of the above applicators could effectively be used in the S.P.G.B. procedure.

SUMMARY OF THE INVENTION

It is therefore an object of this invention to provide means for accomplishing the S.P.G.B. which is devoid of the above-noted disadvantages.

Another object of this invention is to provide an S.P.G.B. procedure which is relatively simple to accomplish and which may be conducted by the patient himself without the need of a professional operator.

A still further object of this invention is to provide a method for S.P.G.B. wherein a controlled amount of medication is delivered into the patient's nose.

Yet another object of this invention is to provide an S.P.G.B. procedure wherein little or no trauma will result because of in and out fashion of the use of a single flexible applicator.

Still another object of this invention is to provide an S.P.G.B. procedure wherein the spraying action will hit all the structures surrounding the S.P.G.B. area so it is sure to hit the area to affect the SPG block accurately.

Yet still another object of this invention is to provide an applicator for the S.P.G.B. that will increase patient comfort and has no systemic side effects that usually accompany the use of analgesics.

Yet still another object of this invention is to provide a reusable applicator with disposable applicator tube attached to a container.

These and other objects of this invention are accomplished, generally speaking, by providing an applicator comprising a housing for holding the lidocaine or other medication. This medication is delivered from the housing through a flexible applicator tube which has a depth stopper and a depth indicator built into it to the treated area in a precise amount to accomplish the SPB block without adverse side effects to the patient such as significant blood pressure drop, the throat or the nose. It is critical to this invention that from about 1/16 cc to about ⅜ cc of lidocaine be delivered to the treated area. If less than this amount is delivered, the SPG block will not be accomplished, if more than this amount is delivered it could cause serious adverse effects such as hypotension leading to shock, throat irritation or nasal trauma. The concentration of lidocaine to be used can range from 1% to 20%. We prefer 20% because of the volume being limited to 1/16 cc to ⅜ cc range and we use 0.1 cc of 20% lidocaine giving a 20 mg dosage delivery per activation of the applicator to tailor individual dosage to individual patient. While the term "lidocaine" is used in the specification and claims, it is intended to include and cover any medication that will accomplish the SPG block. Any applicator capable of delivering this precise amount may be used. However, it must produce also a shotgun-like jet stream directed at the dead end area in the nose and also on applicator tube that can tell the patient whether he or she is using the device correctly.

The SPG block is effective in controlling chronic pain in patients via the pledget delivery method as described in the literature cited. The present invention replaces the pledget delivery method since there are several inherent drawbacks present in the pledget procedure. If the cotton swabs miss the appropriate area, or if too much medication is applied the procedure could be ineffective or cause side reactions. Also, the cotton applicators must be retained in the patient's nose for at least 30 minutes and must be administered by a medical professional. The cotton pledget has been known to fall off from the applicator stick causing a major effort to extract the cotton pledget from the nasal cavity. It would be very desirable to have available a method that can be done at home. The present procedure will deliver a jet stream droplet spray to the pterygopalatine fossa where the SPG block has been done in the past. The procedure of this invention can be used by the patient at home with proper education and training. This treatment modality will decrease the need of analgesic medication use, and minimize the unwanted side effects resulting from systemic drug use. Topical use of lidocaine has little or not systemic effects and the analgesic effect of SPG block may last for a week a longer as described in the literature.

Since the S.P.G.B. procedure can be very painful and heretofore has taken a considerable amount of time, is is important that the procedure be done properly the first time. To repeat the procedure could cause the patient discomfort and perhaps result in some adverse side effects. The procedure of the present invention increases the degree of success of this procedure on the initial try many magnitudes from the previously used systems such as the cotton pledget application. First, the type of applicator is designed to cause a minimum amount of discomfort and pain. Secondly, the jet spray application substantially improves the contact with the appropriate area which is pterygopalatine fossa. Thirdly, and probably most important, is that a controlled amount of medication (lidocaine) is applied to the treated area. As earlier discussed a measured volume of about 1/16 cc to about ⅜ cc must be applied. Below this amount is not an effective dosage. Liquid is preferred, however, gases, gels, viscous solutions or any other suitable form of medication may be used. If a gas is used it may be used in the form of a mist or plasma. Above this amount could cause serious side effects in the throat and nose. Any suitable device capable of delivering a precise measured amount of medication can be used in the procedure of this invention such as hair spray means, pressurized gas propellants, or a pumping unit, all of which must deliver a precise measured amount of medication. Specific suitable devices are like the Nostrilla spray unit (Nostrilla is a registered trademark of Boehringer Ingelheim Pharmaceuticals Inc. of Ridgefield Ct. 06877). However, for clarity, some apparatuses and devices suitable for the procedure of this invention will be described. The medication can be in the form of a liquid or gel or other suitable form.

BRIEF DESCRIPTION OF DRAWING

FIG. 1 is a perspective view of a container device suitable for applying a spray in the procedure of the invention.

FIG. 2 is a perspective view of an applicator tube to be used with the device of FIG. 1.

FIG. 3 is a perspective view of the device of this invention as it is in place during treatment.

DETAILED DESCRIPTION OF DRAWING AND PREFERRED EMBODIMENT

In FIG. 1, a container 1 capable of holding lidocaine or other medication is shown having at its bottom portion a thumb placement recess 2. At the opposite terminal portion of container 1 is a pump spray means 3 capable of dispensing a measured amount of lidocaine through outlet opening 4. This is important to the present invention since an effective amount needs to be applied, while an over dosage will cause medication to drip down into the throat impairing the swallowing reflex and causing fluid to go into the lung. If this were to occur aspiration pneumonia could easily result. This applicator has a one way valve spraying action that will prevent retrograde suction of nasal cavity content back into the bottle. Outlet opening 4 has a flared cut out portion or grooves 5 adapted to receive and fix therein tube attachment 6 (see FIG. 2). Pump spray means 3 comprises a main cap nozzle portion 7 which can be attached onto container 1 or otherwise attached thereto. On either side of cap nozzle portion 7 and attached thereto are finger rings 8 and 9 to facilitate a pumping action. When the patient wishes to carry out the procedure of this invention he or she places the forefinger and middle finger in rings 8 and 9 and the thumb in recess 2. By pushing down on finger rings 8 and 9 and up on thumb recess 2 a precise measured amount of lidocaine is dispensed through outlet opening 4. While the illustrated structure sets out the preferred embodiment, any suitable means to dispense from about 1/16 c.c. to about ⅜ c.c. may be used. Cap 7 may be attached onto container 1 at its opening 10 after the medication is put into container 1. The container 1 and cap 7 may be made from any suitable materials such as plastics, glass or other materials. It is important that these materials be relatively inert to the medication to be used. If pressurized canisters or other devices are capable of dispensing a measured amount of medication and are suitable in all other aspects, they may also be used as a dispensing means.

In FIG. 2 a disposable flexible tube 11 is illustrated having an arrow-like attachment 6 near one terminal portion. This attachment 6 provides convenient means for insertion into opening flared portion 5 of cap 7. It not only provides the user with easy attachment means but also attachment 6 fits tightly into flared opening 5 and securely holds the tube 11 in place during usage. The arrow-like attachment also serves as a reminder to the patient to aim at the lateral side of the nose when spraying for the left or right sided pterygopalatine fossa. The instruction will be, after the insertion of the tube 11 and check for optimal placement using the depth stopper 19 and the depth indicator 20 as a guide, the arrow-like attachment should aim at the left eye if the patient is spraying through the left nostril. This way the tube will spray at the lateral wall of the nose. The patient should aim for the right eye when spraying for the right sided pterygopalatine fossa in the same manner. It is important that all elements of the dispensing means be hermetically sealed to prevent any contamination of the medicine. Attachment 6 also insures that the entire system is air-tight and provides maximum protection against contamination. At the terminal end 13 of tube 11 and on the end opposite from the location of attachment 6 is a soft foam tip 12 to provide extra comfort to the patient. Also, this soft foam tip will be wetted with water to act as a lubricated plug for creating a sealing effect when it wedges between the nasal septum and the lateral wall of the nose. This will help minimized backflow of sprayed fluid to drip down to the throat. Obviously, the material of this foam must be chemically inert to the medication. While it is preferred that the attachment 6 be of triangular configuration, it can be in any suitable form that provides the properties above outlined for this attachment. The diameter of tube 11 should not exceed about 1/16 inch diameter so that it can be conveniently inserted into the nose. Attachment 6 can be secured to tube 11 in any suitable manner. The diameter of the end 14 tube and the diameter of nozzle opening 4 should be such that tube 14 fits snuggly into opening 4 without any leakage. As medication is pumped from container 1 through opening 4 into tube 11 and out end 13, it emerges as a jetstream delivering fine droplets to the area of the pterygopalatine fossa. Jetstream application is important since it extends medication over a substantially wider range than the heretofore used pledget procedure and increases significantly the percent success rate of this procedure. Immediately after the lidocaine is applied, tube 11 is removed from the nose. On tube 11, there are two protruding plastic rods or filaments attached to it at 180° to each other; this is the depth stopper 19. The depth stopper locates at 2¼ inches (5.5 cm) away from the soft foam tip end 13. The purpose of this depth stopper is to limit the length of insertion of the tube into the nose. If the depth stopper touches the nares of the nose, the tube 11 is likely being inserted into the oral pharynx which is the improper location. If this were to occur it would impair the swallowing reflex and cause fluid to go into the lungs. If this happens, the tube 11 should be withdrawn and reinserted into the nose with a more upwardly tilted angle.

The depth indicator 20 is a red line circumscribed around the tube 11; it locates at half of the distance from the depth marker 19 to the tip of the tube 13. The purpose of this depth indicator is to tell the patients that the desirable length of the tube 11 suitable for spraying has been accomplished once the depth indicator disappears into their nose after the foam tip 12 has wedged inside their nose. The flexible deformable conduit has features such as filaments or rods 19, arrow piece 6 and marking 20 to guide the user to reach the proximity of the pteryogopalatine fossa by telling the user the direction and angle of insertion, proper placement, proper length of insertion and indication of erroneous insertion. The tip of the flexible deformable conduit 13 where the shotgun-like spray comes out, has a feature of blocking the drainage conduits and therefore stopping the backflow of the sprayed fluid to drip back down to the throat and also has a soft texture 12 to prevent inducing trauma to the nose. This provides ample time for the medication to be absorbed totally into the capillary circulation and minimizes drainage of any excess fluid.

In FIG. 3, the applicator tube 11 is shown in position during the S.P.G.B. procedure and treatment. The procedure time is reduced from about 30 minutes for the pledget method, to about 1 minute with the present invention. Once attachment 16 is inserted into the medicine-containing vessel 1, and the system is hermetically sealed, lidocaine can be sprayed in a measured quantity into the pterygopalatine fossa area to complete the block. The spray (preferred embodiment) is administered easily by the patient with an extremely high degree of success. With the prior art procedures it would be necessary to have a trained medical professional conduct the procedure with not nearly the success rate as in the present invention. Area 15 is the lateral wall of the nose, area 16 is the middle turbinate and area 17 is the hard palate. The pterydopalatine fossa 18 which houses the sphenopalatine ganglion is the area to be medicated by the procedure of this invention.

A unit dose attachment 21 can be used integral with the flexible plastic applicator tube 22 to deliver a jell or viscous form of lidocaine which is housed in attachment 21 to the appropriate area of the nose to effect the SPG block. The jell and viscous form of lidocaine will stick to the general area where the SPG ganglion lies and the drug will not run down to the throat of the patient to cause problems. The quantity of drug is very important so that the dead end area of the nose will be filled to produce a continuous diffusion of anesthetic to block the SPG ganglion. A suitable amount to the patient's medical condition is administered.

The activation means can be a squeezable or resilient containing vessel as shown in FIG. 4, or a spray means as shown in FIG. 3, or other suitable activation means. In FIG. 4, the containing vessel and the activation means are the same unit.

The preferred and optimumly preferred embodiments of the present invention have been described herein and shown in the accompanying drawing to illustrate the underlying principles of the invention, but it is to be understood that numerous modifications and ramifications may be made without departing from the spirit and scope of this invention.

What is claimed is:

1. A process for accomplishing the Sphenopalatine Ganglion Block in a patient which comprises inserting a flexible tube in an air tight manner to a containing vessel having a measured amount of lidocaine therein and capable of delivering a jet stream spray of its contents, said lidocaine having a concentration of from about 1% to about 20%, inserting said tube into said patient's nose until the frontal terminal portion of said tube reaches the pterygopalatine fossa area, delivering an amount from about 1/16 c.c. to about ⅜ c.c. of said lidocaine from said containing vessel to said ptyergopalatine fossa area via said tube, maintaining said tube in said patient's nose until said amount of lidocaine is completely delivered in spray form to said area.

2. The process of claim 1 wherein said containing vessel is attached to said flexible tube.

3. The process of claim 1 wherein said containing vessel is co-extensive with said flexible tube.

4. The process of claim 1 wherein about 0.1 c.c. of lidocaine per activation is administered in said area with the employment of at least one activation.

5. The process of claim 1 wherein about 1/16 c.c. of lidocaine is sprayed in said area.

6. The process of claim 1 wherein about ⅜ c.c. of lidocaine is sprayed in said area.

7. The process of claim 1 wherein said lidocaine is in liquid form.

8. A process for accomplishing the Sphenopalatine Ganglion Block in a patient which comprises, providing a flexible tube in an air tight manner to a containing vessel having a measured amount of lidocaine therein and capable of delivering lidocaine as a gel, said lidocaine having a concentration of from about 1% to about 2%, inserting said tube into said patient's nose until the frontal terminal portion of said tube reaches the pterygopalatine fossa area, delivering an amount from about 1/16 c.c. to about ⅜ c.c. of said lidocaine from said containing vessel to said ptyergopalatine fossa area via said tube, maintaining said tube in said patient's nose until said amount of lidocaine is completely delivered in gel form to said area.

* * * * *